(12) United States Patent
Loyd et al.

(10) Patent No.: US 8,162,872 B2
(45) Date of Patent: Apr. 24, 2012

(54) TAMPON APPLICATOR WITH RIDGES AND MULTIPLE PETALS

(75) Inventors: Adrienne Rae Loyd, Neenah, WI (US); Steven Anthony Moore, Appleton, WI (US); Marcus David Weiher, Sherwood, WI (US); Thomas William VanDenBogart, Slinger, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1117 days.

(21) Appl. No.: 11/322,443

(22) Filed: Dec. 29, 2005

(65) Prior Publication Data

US 2007/0156080 A1 Jul. 5, 2007

(51) Int. Cl.
*A61F 13/00* (2006.01)
(52) U.S. Cl. .......................... 604/15; 604/16
(58) Field of Classification Search ............. 604/11–18, 604/904, 59
See application file for complete search history.

(56) References Cited

U.S. PATENT DOCUMENTS

| | | | |
|---|---|---|---|
| 4,536,178 A * | 8/1985 | Lichstein et al. ............ 604/15 |
| 5,346,468 A * | 9/1994 | Campion et al. ............ 604/13 |
| 5,348,534 A | 9/1994 | Tomaszewski et al. |
| 5,558,631 A | 9/1996 | Campion et al. |
| 5,569,177 A | 10/1996 | Fox et al. |
| 5,693,009 A | 12/1997 | Fox et al. |
| 5,766,145 A | 6/1998 | Fox et al. |
| 5,800,377 A | 9/1998 | Campion et al. |
| 6,045,526 A * | 4/2000 | Jackson ............ 604/15 |
| 6,056,714 A | 5/2000 | McNelis et al. |
| 6,610,025 B2 | 8/2003 | Berg et al. |
| 6,652,477 B2 | 11/2003 | Karapasha et al. |
| 6,673,032 B2 * | 1/2004 | Buzot ............ 604/15 |
| 7,226,436 B2 * | 6/2007 | Gorham et al. ......... 604/385.17 |
| 2001/0049487 A1 | 12/2001 | Buzot |
| 2002/0143287 A1 | 10/2002 | Buzot |
| 2003/0236485 A1 * | 12/2003 | Fedyk et al. ............ 604/11 |
| 2003/0236499 A1 | 12/2003 | Fedyk et al. |
| 2004/0054317 A1 | 3/2004 | Lemay et al. |
| 2004/0102220 A1 | 5/2004 | Kurita et al. |
| 2005/0015041 A1 | 1/2005 | Karapasha |
| 2005/0020964 A1 | 1/2005 | Melvin et al. |
| 2007/0032758 A1 * | 2/2007 | Chase et al. ............ 604/12 |

FOREIGN PATENT DOCUMENTS

| | | |
|---|---|---|
| WO | WO 01/00127 A1 | 1/2001 |
| WO | WO 01/97735 A1 | 12/2001 |
| WO | WO 02/00153 A1 | 1/2002 |
| WO | WO 03/032883 A1 | 4/2003 |
| WO | WO 2004/000165 A2 | 12/2003 |

OTHER PUBLICATIONS

Patent Cooperation Treaty Search Report from the International Search Authority, International Application No. PCT/US 2006/043010 dated Sep. 6, 2007.

* cited by examiner

*Primary Examiner* — Lynne Anderson

(74) *Attorney, Agent, or Firm* — Randall W. Fieldhack; David J. Arteman

(57) ABSTRACT

The present invention provides an improved tampon applicator having a grip area which provides the user better gripping ability. The grip area may be an area between two ridges on the outer tube of the applicator. In the alternative or in addition to the ridges, the grip area may be a raised pattern which is raised by a distance of between about 0.10 mm and about 0.75 mm. The present invention also provides an improved petal design for a tampon applicator. In this embodiment of the present invention, the petals are separated from each other on all sides by a non-linear gap and the gap is not parallel with the longitudinal axis of the tampon applicator.

42 Claims, 4 Drawing Sheets

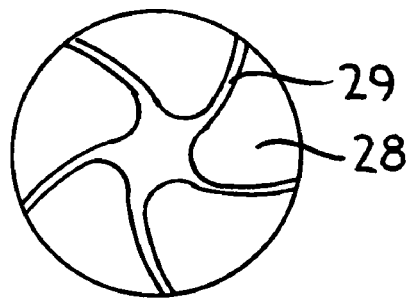
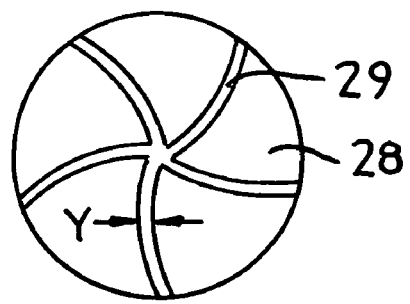
FIG. 7　　　　FIG. 8
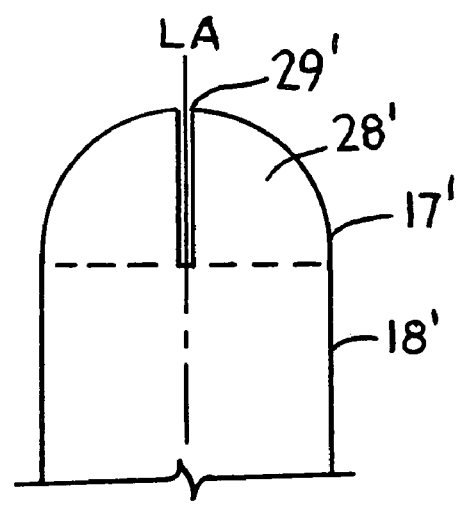
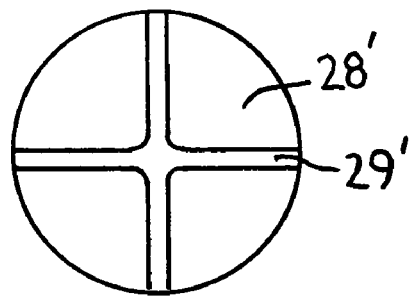
FIG. 9
PRIOR ART
FIG. 10
PRIOR ART

TAMPON APPLICATOR WITH RIDGES AND MULTIPLE PETALS

FIELD OF THE INVENTION

The present invention relates to a tampon applicator.

BACKGROUND OF THE INVENTION

There are two basic types of catamenial tampons used for feminine hygiene currently available on the market. The first type is a digital tampon which is designed to be inserted into a woman's vagina directly by the user's fingers. The second type is a tampon which is designed to be inserted with the aid of an applicator. Typically, tampon applicators have two tubes which are telescoped in one another. Generally, the two tubes are an outer tube, sometimes referred to as the tampon housing tube or inserter tube, and an inner tube, which is sometimes referred to as the plunger tube. The outer tube serves to house or store the tampon prior to use and the inner tube is free to move inside the outer tube and serves to expel the tampon from the outer tube. To use the tampon applicator, the outer tube of the applicator with the tampon contained therein is inserted in the vagina of the user. A force is applied to the inner tube in the direction of the outer tube which causes the inner tube to move inside the outer tube, thereby expelling the tampon from the outer tube into the vagina of the user. Once tampon is expelled, the applicator is then removed by the user from the vagina, leaving the tampon in the vagina of the user.

Currently available tampon applicators are usually provided with a grip area designed to reduce slippage of the applicator in the user's hands. However, the current grip designs only provide reduced slippage in the users hand during one or two of the three stages of tampon insertion with an applicator. That is, current grips only provide slippage protection during insertion of the applicator in the user's vagina, during the expelling process or during removal of the tampon applicator. There is not a currently available tampon on the market which will provide reduced slippage protection during all three stages of inserting a tampon in a user's vagina. For example, some currently available tampon applicators provide an outer tube which has a larger diameter in the portion of the outer tube which has the tampon located therein and a grip area which has a diameter which is smaller than the diameter of the portion of the outer tube which houses the tampon. Some of these two diameter tampon applicators also have a grip area which has an elliptical cross-section or other non-circular shape. While these applicator designs are effective in preventing or reducing slippage of the applicator in the user's hands during insertion of the applicator into the user's vagina, these applicator designs provide virtually no means for preventing or reducing slippage of the applicator during expulsion of the tampon from the outer tube or during removal of the tampon applicator from the user's vagina. Other currently available tampon applicator designs provide protection to the user against slippage or a reduction in slippage in the user's hands during expulsion of the tampon from the tampon applicator or during removal of the tampon applicator from the user's vagina. For example, one currently available design provides a ridge at the end of the outer tube opposite the expulsion end. However, this design does not provide any protection to the user against slippage during insertion of the tampon applicator into the user's vagina. Other tampon applicator designs currently commercially available have raised patterns which are generally raised from the surface of the applicator by less than about 0.25 mm. It has been discovered that this height of the raised pattern is ineffective in preventing or reducing slippage of the tampon applicator in the hands of a user during different stages of inserting a tampon via a tampon applicator.

Further, the technique used to insert a tampon applicator into the vagina, expel a tampon from a tampon application and/or remove the tampon applicator from the vagina, differs from user to user. For example, some users use two hands to insert the tampon applicator into the vagina and expel the tampon from the tampon applicator, while other users use a single hand. Typically, those users who use two hands will grasp the grip area of the tampon applicator between a finger and a thumb, or between the sides of two fingers on one hand and expel the tampon from the tampon applicator by using a finger or a thumb on the other hand. Typically, those users who use a single hand to insert the tampon applicator into a body cavity and expel the tampon from the tampon applicator, will often grasp the grip area of the tampon applicator between the sides of two fingers and use the thumb on the same hand to push the inner tube to expel the tampon from the applicator. Alternatively, a user who uses one hand may grasp the grip area of the tampon applicator with the thumb and middle finger and expel the tampon by pushing the inner tube with the index finger. Other techniques for insertion of the tampon into the vagina may also be used. Each of these methods presents separate issues for use of the tampon applicator in terms of slippage. For example, slippage of the hand or fingers holding the grip area during insertion and removal of the tampon applicator into a body cavity can result in the users hand hitting sensitive parts of the body or resulting in cuts or lacerations due to fingernails or jewelry present on the users hands coming into contact with the body of the user. Slippage during expulsion of the tampon from the applicator can result in similar injuries and can also result in the tampon applicator being pushed too far into the user's body, resulting in an internal injury to the user.

As a result, there is a need in the art for a tampon applicator which has grip areas that will provide protection against slippage in the hands of a user during each of insertion of the tampon applicator into the user's vagina; expulsion of the tampon from the tampon applicator; and removal of the tampon applicator from the vagina. In addition, there is a need in the art to provide a tampon applicator which will provide reduced slippage or slippage protection to the user no mater how the tampon applicator is held in the grip area during use. The present invention provides a tampon applicator which will provided protection against slippage during the insertion of the tampon applicator into the vagina, the expulsion of the tampon from the tampon applicator into the vagina and the removal of the tampon applicator from the vagina after the tampon has been expelled.

Some currently available tampon applicators have an insertion tip at the explusion end of the outer tube of the applicator. The insertion tip typically has four or more petals and the petals are generally formed with gaps or silts between each of the petals. These gaps or slits are typically parallel with the longitudinal axis of the tampon applicator and are linear. The currently available tampon applicators with an insertion tip typically have petals which are designed to be thin and flexible, to provide for smooth insertion of the tampon applicator into the user's vagina. The petals are designed to open with minimal force so that when the tampon is expelled from the applicator, the petals do not provide a large resistance that makes it difficult to remove the tampon from the tampon applicator. However, the currently available petal designs do create problems for some users. The currently available petals are perceived by users to be sharp and there is a potential that the petals could cause an injury, such as scraping, or scratching, to the vagina or external body tissue, such as the labia, during insertion. In addition, some users complain that the current petal designs result in pinching the vagina when the petals close after the tampon is expelled from the applicator. This may be a result of some of the currently available tampon applicators which have petals which may overlap one another before or during insertion into the vagina. As a result, there is a need in the art for a new petal design which will be perceived by the user to be softer, more comfortable, more flexible and less likely to pinch or otherwise injure the user's vagina and other sensitive body structure in the vaginal region of a user.

SUMMARY OF THE INVENTION

Generally stated, the present invention provides a tampon applicator having a first member capable of holding a tampon and having a shape suitable for insertion into a body cavity of a user. The first member has an outer surface, a longitudinal axis, a caliper measured perpendicular to the longitudinal axis, and an expulsion end which is adapted to allow expulsion of the tampon held in the first member from the first member. This first member also has a second end which is distal to the expulsion end of the first member. The first member further has a grip region located on the outer surface of the first member located near the second end. This grip region, in this embodiment of the present invention, has a first ridge and a second ridge extending from the outer surface of the first member. The first and second ridges each essentially encircle the first member in a direction essentially perpendicular to the longitudinal axis of the first member. The two ridges are separated by a distance which allows a tip of a user's finger to fit between the first ridge and the second ridge. This distance between the first ridge and the second ridge defines a grip area for the tampon applicator; the grip area has a caliper which is equal to or greater than the caliper of the first member outside the grip area. In addition, the first and second ridges each have a caliper measured perpendicular to the longitudinal axis of the first member which is greater than the caliper of each of the first member and grip area. The applicator also has a second member telescopically and slidably mounted in the first member at the second end of the first member. The second member is adapted to expel a tampon held in the first member from the first member through the expulsion end of the first member. In this embodiment of the present invention, the grip area may also have a raised portion which is raised above the surface of the grip area by a distance between 0.10 mm and 0.75 mm.

In another embodiment of the present invention, provided is a tampon applicator having a first member capable of holding a tampon and having a shape suitable for insertion into a body cavity of a user. The first member has an outer surface, a longitudinal axis, and an expulsion end which is adapted to expel a tampon held in the first member from the first member. This first member also has a second end which is distal to the expulsion end of the first member. The first member further has a grip region located on the outer surface of the first member which is located near the second end. The grip region has a first surface and a raised surface, wherein the raised surface extends a distance between 0.25 mm and 0.75 mm above the first surface of the grip region. The applicator also has a second member telescopically and slidably mounted in the first member at the second end of the first member. The second member is adapted to expel a tampon held in the first member from the first member through the expulsion end of the first member.

The present invention also provides a tampon applicator having a first member capable of holding a tampon and having a shape suitable for insertion into a body cavity of a user. The first member has an outer surface, a longitudinal axis, an expulsion end which is adapted to expel a tampon held in the first member from the first member. In addition, the first member has a second end which is distal to the expulsion end of the first member. The applicator also has a second member which is telescopically and slidably mounted in the first member at the second end of the first member. The second member is adapted to expel a tampon held in the first member from the first member through the expulsion end of the first member. In this embodiment of the present invention, the applicator also has an insertion tip located on the expulsion end of the first member. The insertion tip has a generally dome shape prior to use and has at least 3 petals, and with each petal extending from the expulsion end of the first member. Each petal is separated from the other petals by a distance on all sides of each petal, and the separation of each of the petals is non-linear when the petals are in the generally dome shape.

BRIEF DESCRIPTION OF THE DRAWINGS

FIG. 7 shows a top view of an insertion tip of the present invention having petals separated by a non-linear gap or slit.

FIG. 8 shows a top view of an alternative insertion tip of the present invention separated by a non-linear gap or slit.

FIG. 9 shows a partial side view of a conventional tampon applicator known to those skilled in the art.

FIG. 10 shows a top view of a conventional insertion tip currently used in commercially available tampon applicators known to those skilled in the art.

DEFINITIONS

It should be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

As used herein, the term "tampon" is generally referred to as a vaginal tampon, which is inserted into the vagina of a female user to absorb menses, blood and other bodily fluids form the user's vagina. Similarly, the term "tampon applicator" is generally referred to in this specification as a vaginal tampon applicator. It should be understood, however, that the tampon and applicator described herein is applicable to other types of tampons such as, without limitation, medical tampons, dental tampons, surgical tampons, nasal tampons, and the like.

DETAILED DESCRIPTION OF THE INVENTION

To obtain better understanding of the embodiments of the present invention, attention is directed to the Figures.

Figure 1:
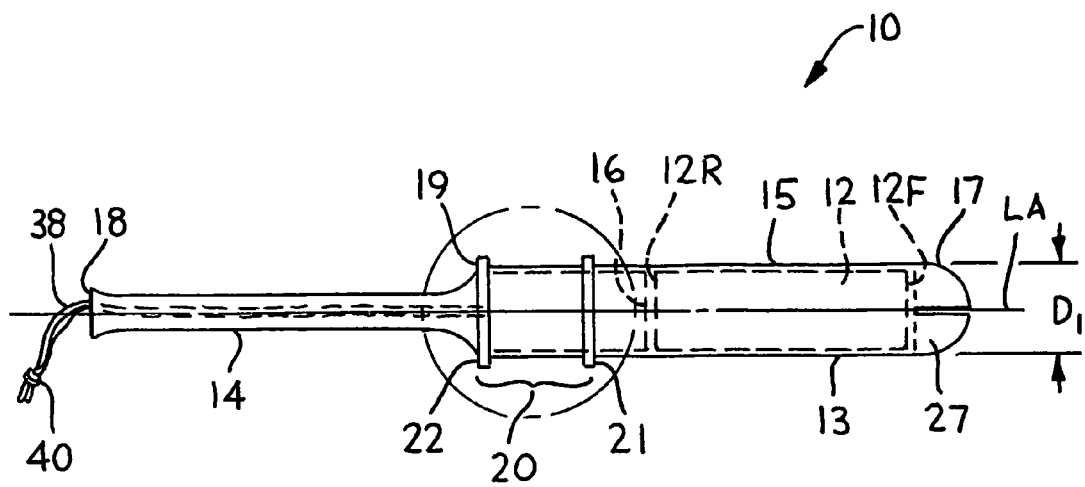
FIG. 1 shows a side elevation of a tampon applicator of the first embodiment of the present invention.
Figure 3:
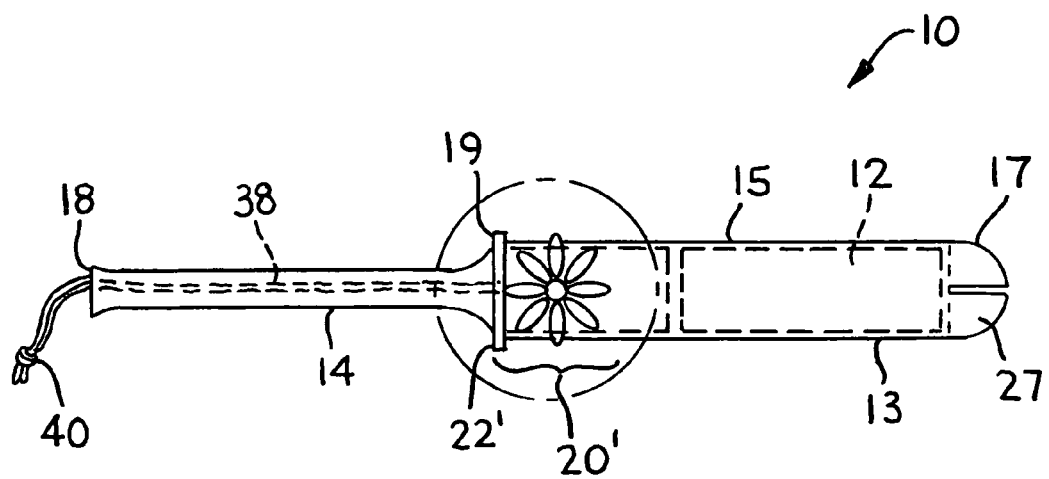
FIG. 3 shows a side elevation of a tampon applicator of the second embodiment of the present invention.
Figure 5:
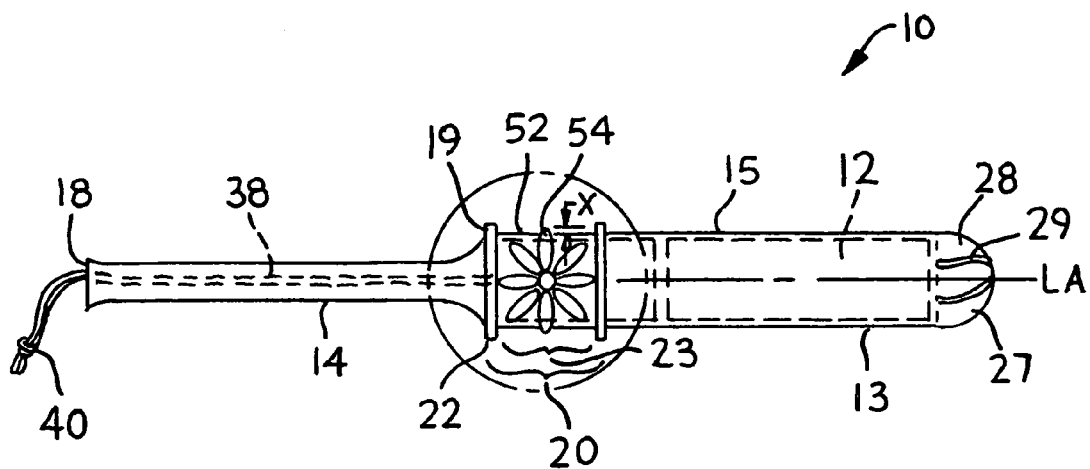
FIG. 5 shows a side elevation of a tampon applicator having features from both the first and second embodiments of the present invention.

Referring to FIGS. 1, 3 and 5, shown is a tampon applicator 10 which is design to hold a tampon 12 prior to use. The tampon applicator 10 is designed to provide a comfortable and safe means for inserting the tampon 12 into a body cavity of a user, in particular the vagina of a female user. The tampon 12, as illustrated in FIGS. 1, 3 and 5, has a generally cylindrical fibrous body that is sized and shaped for insertion into a women's vagina during her menstrual period to absorb menses, blood, and other body fluids. The front end of the tampon 12F, which is sometimes called the forward end or the explusion end, may have a number of different shapes, including, but not limited to a blunt, rounded, semi-spherical, ellipsoidal or conical. The tampon 12 includes a withdrawal string 38 that is fastened to the body of the tampon 12 generally adjacent a rear end 12R of the tampon 12, which is sometimes called the trailing end of the tampon 12. The string 38 is used to pull the tampon 12 from the female user's vagina. Generally, the withdrawal string is attached to the tampon 12 by looping the withdrawal string through the tampon or may be attached using other methods, such as, sewing or bonding the string to the fibrous structure of the tampon 12 using known bonding techniques. The withdrawal string may also be provided with a knot 40 which assures that the string 38 does not separate from the tampon 12. The body of the tampon 12 is made of absorbent materials such as absorbent fibers, including natural and synthetic fibers, compressed into a unitary body of a size that may easily be inserted into the vaginal cavity. Suitable fibers include, for example, cellulosic fibers such as cotton and rayon. Fibers may be 100% cotton, 100% rayon, a blend of cotton and rayon, or other materials known to be suitable for tampon use. The body of the tampon 12 has a generally elongated cylindrical shape so that it has a sufficiently large body of absorbent material to provide the required absorbing capacity. It is understood that the tampon body may be made in a variety of shapes, besides cylindrical.

The tampon 12 may also include a cover (not shown) surrounding the fibrous body. The cover prevents the fibers of the tampon body from directly contacting the inner walls of a woman's vagina. This assures that no fibers will be left behind in the vagina after the tampon 12 is removed. The cover can be tucked into ends of the body of the tampon so as to completely surround and enclose the fibers. The cover can also be constructed from a heat-sealable material to assist in bonding it to the fibers, such as by heat and/or pressure. The cover can be formed from a nonwoven material such as a polyolefin, particularly polypropylene or polyethylene. A suitable material is a spunbond material. Suitable methods and materials for the production of tampons are well known to those skilled in the art.

The tampon applicator 10 of the present invention has a first member 13 capable of holding a tampon 12. The first member 13 has a shape which is suitable for inserting the tampon applicator 10 into a body cavity of a user, such as, in the case of vaginal tampons, into the vagina of a female user. The first member has an outer surface 15, a longitudinal axis LA, a caliper D, measured perpendicular to the longitudinal axis LA, and an expulsion end 17. The expulsion end 17 is adapted to expel a tampon 12 from the first member 13. The expulsion end 17 may be open, be covered with a film-like material or may be provided with an insertion tip 27, which is shown in FIGS. 1, 3 and 5. The insertion tip may be any insertion tip known to those skilled in the art, which will be discussed in greater detail below, or can be the insertion tip 27 of another embodiment of the present invention, which is also discussed in greater detail below. The first member 13 also has a second end 19 which is distal to the expulsion end 17 of the first member.

In the present invention, the first member 13 is generally a hollow tube having a generally cylindrical shape. Other shapes may be used for the first member, but from the standpoint of ease of insertion and ease of production, it is desired that the first member 13 have a generally cylindrical shape. By "generally cylindrical", it is meant that the cross-section of the first member is circular in nature. It is possible, that the first member is tapered such that the caliper or diameter $D_1$ of the first member gradually increases from the expulsion end 17 to the second end 19. If a tapered first member is used, it is desirable that the interior diameter of the first member 13 not vary by more than 2 mm over the length of the first member for aesthetic reasons. The caliper or diameter of the first member outside the grip area 20 should generally be in the range of about 8 mm to about 20 mm, for human catamenial tampons. Various factors, such as the size or absorbency of the tampon to be expelled, can be used to determine the appropriate caliper or diameter of the first member 13. In the case of larger animals, the size of the tampon and the applicator could be increased. In a similar manner, in the case of a nasal tampon or tampons for smaller animals, the size of the tampon and applicator could be reduced. The first member 13 is commonly referred to in the art as an "outer tube", "inserter tube" or "housing tube". These terms are interchangeable with one another.

The applicator also has a second member 14 telescopically and slidably mounted in the first member 13 at the second end 19 of the first member. The second member 14 of the applicator is commonly known as the "plunger" or "inner tube". As with the first member 13, the second member 14 is also generally hollow. The second member 14 of the tampon applicator has a first end 16 which is adapted to expel the tampon from the first member 13, when a force is applied to the second end 18 in a direction towards the first member 13. The first end 16 of the second member 14 is mounted in the first member 13 by having the second member 14 have, at least on along the length of the second member inside the first member 13, a diameter which is approximately equal to the inner diameter of the first member 13. This will prevent the second member from losing its telescopic relationship with the first member. Other ways of ensuring that the second member will remain in a telescopic relationship with the first member, known to those skilled in the art, may also be used. In addition, the second member 14 and the interior of the first member may have complementary mechanisms which help retain the second member 14 inside the first member 13 or prevent the second member 14 from becoming dislodged from the first member 13.

As a force is applied to the second end 18 of the second member 14 in a direction towards the first member 13, the second member 14 is pushed into the first member 13, forcing the tampon 12 to be expelled from the first member 13 from the expulsion end 17 of the first member. As is shown in FIGS. 1, 3 and 5, the tampon withdrawal string 38 may be threaded through the second member such that the knot, if present, is visible outside the second member.

The first and second members 13, 14, making up the tampon applicator of the present invention, may be prepared from a wide variety of materials, including those materials which have been conventionally used in the art for tampon applicators. However, from the standpoint of user comfort, it is desirable that the first and second members 13, 14 of the tampon applicator 10 are prepared from a thermoplastic resin.

Suitable thermoplastic materials include, for example, polyolefins, such as low density polyethylene and low density polypropylene, polyesters, polyurethanes, ethylene vinyl acetate and polystyrene or the like. Other materials may be used including biodegradable polymer such as polylactic acid or polyvinyl alcohol. When the surface of the exterior of the outer tube 13 is smooth and/or slippery, the outer tube 13 will easily slide into a woman's vagina without subjecting the internal tissues of the woman's vagina to abrasion. The outer tube 13 may be coated to give it a high slip characteristic. Wax, polyethylene, a combination of wax and polyethylene, cellophane, and clay are representative coatings that can be applied to the exterior layer to facilitate comfortable insertion. The illustrated outer tube 13 is a straight, elongated cylindrical tube. It is understood however that the applicator 10 could have different shapes and sizes than those illustrated and described herein.

The first member 13 further has a grip region 20 located on the outer surface 15 of the first member located near the second end 19. This grip region 20, in the first embodiment of the present invention, has a first ridge 21 and a second ridge 22 extending from the outer surface 15 of the first member 13. The first ridge 21 and the second ridge 22 each essentially encircle the first member in a direction generally perpendicular to the longitudinal axis LA of the first member 13. The first ridge 21 and the second ridge 22 are separated by a distance $D_r$. This distance $D_r$ is sufficiently large enough to allow a tip of a user's finger to fit between the first ridge 21 and the second ridge 22. This distance between the first ridge 21 and the second ridge 22 defines a grip area 23 for the tampon applicator 10 of this embodiment of the present invention. The grip area 23 has a caliper or diameter $D_2$ which is equal to or greater than the caliper or diameter $D_1$ of the first member 13 outside the grip region 20. In addition, the first ridge 21 has a caliper or diameter $R_1$ and the second ridge 22 has a caliper or diameter $R_2$, each of $R_1$ and $R_2$ being measured in a direction perpendicular to the longitudinal axis LA of the first member 13. The caliper or diameter $R_1$ and $R_2$ of the first and second ridges is greater than the diameter $D_2$ of the first member 13 in the grip area 23 and the diameter $D_1$ of the first member 13 outside the grip area.

As is stated above, the first and second ridges 21, 22 generally encircle the first member 13 in the grip region 20. These ridges may be continuous around the circumference of the first member 13 or the ridges may be discontinuous, i.e. having spaces or gaps between the arcs of the ridges. If the ridges are discontinuous, it is desirable that the at least 50% of the circumference of the first member at the ridge location has a ridge. Ideally, at least 75% of the circumference of the first member at the ridge location has a ridge. Most desirably, the first and second ridges are continuous around the circumference of the first member. In an alternative embodiment, the ridges may have an ornamental design rather than being circular in nature. For example, ridges may have a wavy look to them or the ridges could have other patterns not specifically mentioned herein.

Figure 2:
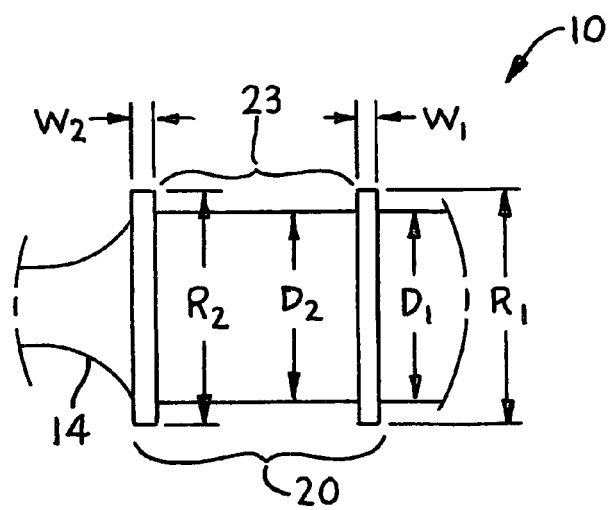
FIG. 2 shows an enlargement of the grip area of the tampon applicator shown in FIG. 1 within the circle line 2 of FIG. 1.

In the first embodiment of the present invention shown in FIGS. 1 and 2, the first and second ridges 21 and 22 are shown having a width $W_1$ and $W_2$, respectively. In the present invention, the width of each of $W_1$ and $W_2$ may be the same or different and are generally between 0.5 mm and 2.5 mm. If the width is less than about 0.5 mm, the ridge will begin to feel sharp to a user. If the width is greater than about 2.5 mm, no additional advantage is obtained and the amount of material needed to make the outer tube will increase, thereby increasing the cost of the applicator. In one embodiment of the present invention, the width of each of $W_1$ and $W_2$ is between about 0.75 mm and about 2.0 mm. Ideally, the width of each of $W_1$ and $W_2$ should be about 1.0 mm to about 1.5 mm.

As is stated above, the distance between the ridges 21 and 22 designated as $D_r$ in FIG. 2 should be about the width of the tip of a finger. In practice, the distance $D_r$ is generally about 10 mm to about 20 mm in length. Ideally, given the size of most females fingers, the distance $D_r$ is generally about 13 mm to about 17 mm in length. If the distance $D_r$ is too far apart, the first ridge will become too close to the expulsion end of the first member and may limit the distance the first member may be inserted into the user's vagina, thereby causing the tampon not to be properly inserted, unless the tampon applicator has a longer outer tube.. If the tampon applicator has a longer outer tube, then it may be difficult for a user to properly grasp the applicator and insert the tampon applicator into the user's vagina, and to properly expel the tampon from the applicator. In addition, if the distance between the ridges is too far apart, the user's fingers could slip within the grip area, causing similar injuries to those discussed above, such as cuts or lacerations to this sensitive area of the female body. If the ridges are too close together, the slip prevention function of the ridges may not be provided for all users.

The diameter $R_1$ and $R_2$ of each ridge 21 and 22, respectively, should each independently be in the range of about 1 mm to about 4.0 mm greater than the diameter $D_1$ of the first member. If the diameter of each of the ridges 21 and 22 is less than 1 mm greater than the diameter $D_1$ of the first member 13, the slip prevention or reduction property of the present invention may not be provided to a desired degree. In addition, if one or both of the ridges 21 and 22 is greater than about 4.0 mm greater than the diameter $D_1$ of the first member 13, the tampon application will begin to have an undesired bulky feel and the increase diameter will make the user perceive that the applicator is actually larger in diameter than it actually is. Ideally, the diameter $R_1$ and $R_2$ of each ridge 21 and 22, respectively, are each independently in the range of about 1.5 to about 2.5 mm greater than the diameter $D_1$ of the first member.

Also, in the first embodiment of the present invention, the caliper or diameter $D_2$ of the grip area 23 may be the same diameter $D_1$ as the first member outside the grip area. Alternatively, the caliper or diameter $D_2$ of the grip area 23 may be equal to or larger than the diameter $D_1$ of the first member outside the grip area. From the standpoint of ease of manufacture, it is desirable that $D_1$ and $D_2$ are approximately equal to one another.

The grip area 23 may be devoid of any designs or may contain ornamental or aesthetically pleasing design. Depending on the height of the design, which will be discussed in further detail below, the ornamental or aesthetically pleasing design may further provide improved gripability of the grip area 23. In the present invention, it is also possible to further improve the gripability of the grip area 23 by applying materials which will increase the coefficient of friction in the grip area. For example, the grip area may have a textured feel or finish, a material having a high wet coefficient of friction, a pressure sensitive adhesive or a combination of one or more of these materials or finishes applied to the grip area. If an ornamental design is placed in the grip area, suitable designs include flowers, rings and the like. Other ornamental designs may include geometric shapes such as arcs, circles, lines, polygon shapes, triangles and the like or combinations of these shapes.

Shown in FIG. 5 is a further embodiment of the first embodiment of the present invention having an ornamental design in the grip region 20. The ornamental design in the grip region 20 may have first surface 52 and a raised surface 54. In this embodiment of the present invention, the raised surface 54 is raised from the first surface by a distance X, wherein the distance X is between 0.15 mm and 0.75 mm above first surface 52 in the grip area 23. It has been discovered that a raised surface 54 in the grip area 23 of a tampon application provides improved gripability of the grip region. Generally, the raised surface is raised above the first surface by a distance X which is between 0.25 and 0.65 mm. More specifically, in an additional aspect of this embodiment of the present invention, the distance X is between 0.35 mm and about 0.50 mm.

Figure 4:
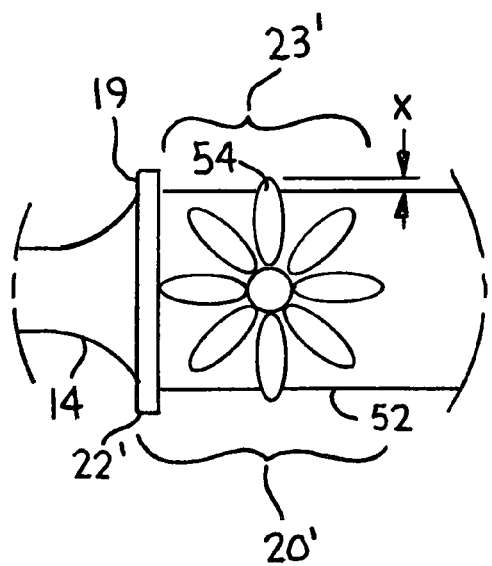
FIG. 4 shows an enlargement of the grip area of the tampon applicator shown in FIG. 3 within the circle line 4 of FIG. 3.

A second embodiment of the present invention is shown in FIGS. 3 and 4. In this embodiment of the present invention, the tampon applicator 10 has a first member and a second member. The description of the first and second members of the tampon applicator, the tampon and other features of the tampon applicator outside the grip region is found above in the description of the present invention and will not be repeated here for brevity. The second embodiment of the present invention is different from the first embodiments of the present invention in that the grip region 20' is different from the grip region 20 of the first embodiment. In this embodiment of the present invention, the grip region 20' is located at or near the second end 19 of the first member 13. The grip region 20' has a grip area 23' located on the outer surface 15 of the first member 13. The grip region 20' has first surface 52 and a raised surface 54. In this embodiment of the present invention, the raised surface 54 is raised from the first surface by a distance X, wherein the distance X is between 0.25 mm and 0.75 mm above first surface 52 in the grip area 23'.

It has been discovered that a raised surface 54 in the grip area 23 of a tampon application provides improved gripability of the of the grip region, when ridges are not used, as in the first embodiment of the present invention. When the raised surface is extended from the surface of the first member at a distance less than 0.25 mm, the raised surface does not impart a desired level of slip resistance and the tampon applicator 10 can slip in a user's hand during insertion into the vagina, during expulsion of the tampon from the tampon applicator and/or during removal of the tampon applicator from the user's vagina. If the raised surface is in excess of about 0.65 mm, the surface may become uncomfortable for a user to grasp during use of the applicator. In one embodiment of the invention, the raised surface 54 extends a distance X above the first surface 54, wherein the distance X is between 0.35 mm and 0.5 mm above the first surface.

The raised surface 54 may be a wide variety of surfaces including embossments, a series of ridges, treads, and the like. The raised surface 54 may be a series of geometric shapes such as arcs, circles, polygons, triangles and the like. Alternatively, the raised surface may be in a pattern of an object which is pleasing to users of vaginal tampons, such as a flower, as is shown in FIGS. 3 and 4. More than one pleasing object may be used in the grip area. To further enhance the gripability of the raised surface, the pattern may be selected such that there are several acute angles in the pattern. Acute angles in the pattern tend to increase the gripability of the raised surface. This is true for the raised surface when the ridges are not present as well as when the ridges of the first embodiment of the present invention are present.

In addition to the raised surface or raised pattern in the grip region, the grip region may have one or more ridges as described above in the first embodiment of the present invention. As is shown in FIGS. 3 and 4, only the ridge 22' located at or near the second end 19 of the first member may be present. In an alternative configuration, the ridge may be located in the grip region closer to the expulsion end of the first member 13 of the tampon application (not shown). In a desired embodiment of the present invention, which is shown in FIG. 5, the first and second embodiments of the present invention are combined to form a tampon applicator having a grip region 20 located on the outer surface 15 of the first member located near the second end 19. This grip region 20 has a first ridge 21 and a second ridge 22 extending from the outer surface 15 of the first member 13. The first ridge 21 and the second ridge 22 each essentially encircle the first member in a direction generally perpendicular to the longitudinal axis LA of the first member 13. The first ridge 21 and the second ridge 22 are separated by a distance $D_r$ (shown in FIG. 2) which is sufficiently large enough to allow a tip of a user's finger to fit between the first ridge 21 and the second ridge 22. This distance between the first ridge 21 and the second ridge 21 defines a grip area 23 for the tampon applicator. Within the grip area is a raised surface 54 or raised pattern 54 which is raised above the first surface 52 of the grip area by a distance X, wherein the distance X is between 0.1 mm and 0.75 mm above first surface 52 in the grip area 23 (shown in FIG. 3).

In a further embodiment second embodiment of the present invention, the raised surface 54 or raised pattern is desirable between about 0.35 mm and about 0.5 mm above the first surface 54. In addition, the raised surface is desirable as an aesthetically pleasing pattern. Further, the diameter, the width and the distance between the ridges 21, 22, if present, should be within the ranges discussed above in regard to the first embodiment of the present invention.

An additional embodiment of the present invention relates to the insertion tip of the tampon applicator. Referring to FIG. 5 for reference to parts of the tampon applicator in this embodiment of the present invention, the present invention also provides a tampon applicator having a first member 13 capable of holding a tampon 12 and having a shape suitable for insertion into a body cavity of a user. The first member 13 has an outer surface 15, a longitudinal axis LA, an expulsion end 17 which is adapted to expel a tampon held in the first member 13 from the first member and a second end 19 which is distal to the expulsion end 17 of the first member. The applicator also has a second member 14 which is telescopically and slidably mounted in the first member 13 at the second end 19 of the first member 13. The second member 14 is adapted to expel a tampon 12 held in the first member 13 from the first member 13 through the expulsion end 17 of the first member. In this embodiment of the present invention, the applicator 10 also has an insertion tip 27 located on the expulsion end 17 of the first member 13. The insertion tip 27 has a generally dome shape prior to use and comprises at least three petals 28. Each petal 28 extends from the expulsion end 17 of the first member 13 and each petal 28 is separated from the other petals by a gap or slit 29 on all sides each petal 28, except the portion of each petal 28 which is attached to the expulsion end 17 of the tampon applicator 10. In this embodiment of the present invention, the separation of each of the petals 28 by the gap or slit 29 is non-linear when the petals are in the dome shape. In addition, the gap or slit 29 between each petal 28 is not parallel with the longitudinal axis LA of the first member 13, when the petals are in the generally dome shape.

Figure 6:
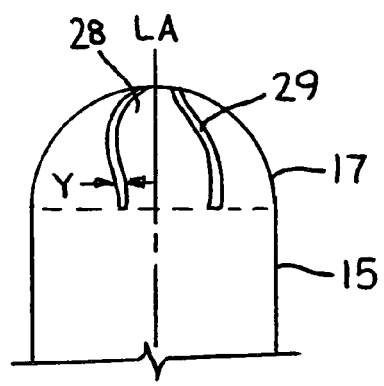
FIG. 6 shows a partial side view of the tampon applicator of the present invention having petals separated by a non-linear gap or slit.

To gain a better understanding of this embodiment of the present invention, attention is directed to FIGS. 6, 7, and 8 as compared to the convention petals shown in FIGS. 9 and 10. As is shown in FIG. 6 as compared to FIG. 9, the petals 28 extending from the expulsion end 17 of the first member 13 of the tampon applicator are separated by a distance or gap 29. The separation, as is shown in FIGS. 9 and 10 is parallel with or runs along the longitudinal axis LA. In clear contrast, the petals 28 of the present invention are separated by a gap or slit 29 which is non-linear and is not parallel with the longitudinal axis LA.

The insertion tip 27 with its petals 28 that are separated with a gap, slit or distance 29 which is non-linear and not parallel with the longitudinal axis of the first member 13 are perceived by the users to be softer, more comfortable, more flexible and less likely to pinch the user's vagina and other sensitive body structure in the vaginal region of a user. As a result, the petal design of the insertion tip provides an emotional benefit to the user which is not provided by the conventional petals. In addition, the petals 28 are aesthetically pleasing to the user since they have a smoother look than conventional petals 28.

In the present invention, the insertion tip will generally have between four and six petals. If there are more than six petals on the insertion tip, the individual petals will become weaker and become more likely to bend out of the plan of the generally dome shape, possibly scratching or otherwise injuring the user during insertion of the tampon applicator into the vagina or when the tampon applicator is withdrawn from the vagina of a user, after expulsion of the tampon. In one embodiment of the present invention, the insertion tip has five petals.

The insertion tip may be separately formed and joined using suitable means to the expulsion end of the first member. In the alternative, the insertion tip 27 is formed integrally with the first member. When integrally formed with the first member of the tampon applicator, the petals of the insertion tip extend from the first member. From a standpoint of ease to manufacture, it is desirable that the insertion tip and petals of the insertion tip be formed integrally with first member. The insertion tip and first member of this aspect of the present invention may be prepared from the same thermoplastic materials described above, usable for preparing the tampon applicator.

The gap 29 between the petals should be set far enough apart such that the petals can not overlap during insertion of the tampon into a user's vagina, after expulsion of the tampon from the applicator or during withdrawal of the tampon applicator from the users vagina. Generally, the distance y between the petals should be between about 0.75 mm and 1.5 mm. If the distance between the petals is too small, the petals may pinch the user of the tampon applicator. If the distance is too far apart, the insertion tip may not protect the tampon before use. Ideally, the distance between the petals should be about 1 mm apart.

The insertion tip described above may also be used in conjunction with the tampon applicators having the grip of the first or second embodiments of the present invention. Alternatively, the insertion tip described above may be used with conventional or known tampon applicators without the grip of the first and second embodiments of the present invention.

Those skilled in the art will recognize that the present invention is capable of many modifications and variations without departing from the scope thereof. Accordingly, the detailed description and examples set forth above are meant to be illustrative only and are not intended to limit, in any manner, the scope of the invention as set forth in the appended claims.

The invention claimed is:

1. A tampon applicator comprising:
   a. a first member capable of holding a tampon and having a shape suitable for insertion into a body cavity of a user, the first member comprising an outer surface, a longitudinal axis, a caliper measured perpendicular to the longitudinal axis, an expulsion end which is adapted to expel a tampon held in the first member from the first member and a second end which is distal to the expulsion end of the first member, the first member further comprises a grip region located on the outer surface near the second end, said grip region comprising a first ridge and a second ridge extending from the outer surface of the first member, wherein the first and second ridges each essentially encircle the first member in a direction essentially perpendicular to the longitudinal axis of the first member, and the second ridge is located at a distance from the first ridge such that a tip of a user's finger can fit between the first ridge and the second ridge, the distance between the first ridge and the second ridge defines a grip area for the tampon applicator, the grip area has a caliper which is equal to or greater than the caliper of the first member outside the grip area and first and second ridges each have a caliper measured perpendicular to the longitudinal axis of the first member which is greater than the caliper of each of the first member and grip area, and wherein the grip area comprises a first surface and a raised pattern;
   b. a second member telescopically and slidably mounted in the first member in the second end of the first member, said second member adapted to expel a tampon held in the first member from the first member through the expulsion end of the first member.

2. The tampon applicator according to claim 1, wherein the first member comprises an elongated tube having a generally cylindrical shape.

3. The tampon applicator according to claim 2, wherein the caliper of the first member, grip area, the first ridge and the second ridge are each a diameter, wherein the diameter of the first and second ridges is larger than the diameter of the first member and the diameter of the grip area.

4. The tampon applicator according to claim 3, wherein the diameter of each of the first and second ridges is at about 1 mm to about 4.0 mm greater than the diameter of the first member.

5. The tampon applicator according to claim 4, wherein the distance between the first ridge and the second ridge is between 10 mm and 20 mm.

6. The tampon applicator according to claim 4, wherein the diameter of at least one of the first and second ridges is about 1.5 mm to about 2.5 mm greater than the diameter of the first member.

7. The tampon applicator according to claim 6, wherein the first ridge has a diameter which is about 1.5 mm to about 2.5 mm greater than the diameter of the first member.

8. The tampon applicator according to claim 6, wherein the second ridge has a diameter which is about 1.5 mm to about 2.5 mm greater than the diameter of the first member.

9. The tampon applicator according to claim 3, wherein each of the first and second ridges continuously encircle the first member.

10. The tampon applicator according to claim 3, wherein the second ridge is located at the second end of the first member.

11. The tampon applicator according to claim 3, wherein the first ridge, the second ridge, and the grip area are integral with the first member.

12. The tampon applicator according to claim 3, wherein each of the first and second ridge has a width in the longitudinal direction of about 0.5 mm to about 2.5 mm.

13. The tampon applicator according to claim 12, wherein each of the first and second ridge has a width in the longitudinal direction of about 0.75 mm to about 2.0 mm.

14. The tampon applicator according to claim 3, wherein the raised pattern extends a distance between 0.15 mm and 0.75 mm above first surface of the grip area.

15. The tampon applicator of claim 14, wherein the raised pattern extends a distance between 0.35 mm and 0.50 mm above the first surface.

16. The tampon applicator according to claim 1, wherein the distance between the first ridge and the second ridge is between 10 mm and 20 mm.

17. The tampon applicator according to claims 16, wherein the distance between the first ridge and the second ridge is between 13 mm and 17 mm.

18. The tampon applicator according to claim 1, wherein the second ridge is located at the second end of the first member.

19. The tampon applicator according to claim 1, wherein the first ridge, the second ridge, and the grip area are integral with the first member.

20. The tampon applicator according to claim 1, wherein the first member is a molded thermoplastic material.

21. The tampon applicator according to claim 1, wherein the first member comprises an elongated tube having a generally cylindrical shape; the caliper of the first member, grip area, the first ridge and the second ridge are each a diameter, wherein the diameter of the first and second ridges is larger than the diameter of the first member and the diameter of the of the grip area; the diameter of each of the first and second ridges is between 1.5 mm and about 2.5 mm greater than the diameter of the first member; the distance between the first ridge and the second ridge is between 13 mm and 17 mm; each of the first and second ridges are continuous around the first member; the first ridge, the second ridge, and the grip area integral with the first member and the first member comprises a molded thermoplastic material.

22. The tampon applicator according to claim 21, wherein each of the first and second ridge has a width in the longitudinal direction of about 0.75 mm to about 2.0 mm.

23. The tampon applicator according to claim 1, further comprising an insertion tip located on the expulsion end of the first member, wherein the insertion tip has a dome shape prior to use and comprises at least 3 petals, each petal extends from the expulsion end of the first member, each petal Is separated from the other petals by a distance on all sides of each petal, and the separation of each of the petals is non-linear when the petals are in the dome shape.

24. The tampon applicator of claim 23, wherein the separation of each of the petals from the other petals is not parallel with the longitudinal axis of the first member when the petals are in the dome shape.

25. The tampon applicator of claim 23, wherein the insertion tip comprises 4-6 petals.

26. The tampon applicator of claim 23, wherein the insertion tip and the petals of the insertion tip are integral with the first member.

27. The tampon applicator according to claim 23, wherein the first member comprises an elongated tube having a generally cylindrical shape.

28. The tampon applicator according to claim 27, wherein the first member and the insertion tip is a molded thermoplastic material.

29. The tampon applicator according to claim 23, wherein the petals are separated by a distance of about 0.75 mm to about 1.5 mm.

30. A tampon applicator comprising:
a. a first member capable of holding a tampon and having a shape suitable for insertion into a body cavity of a user, the first member comprising an outer surface, a longitudinal axis, a caliper measured perpendicular to the longitudinal axis, an expulsion end which is adapted to expel a tampon held in the first member from the first member and a second end which is distal to the expulsion end of the first member, the first member further comprises a grip region located on the outer surface near the second end, said grip region comprising a first surface and a raised pattern, wherein the first surface has a caliper that is equal to or greater than the caliper of the first member outside the grip area, and wherein the raised pattern extends a distance between 0.25 mm and 0.75 mm above the first surface of the grip region; and
b. a second member telescopically and slidably mounted in the first member in the second end of the first member, said second member adapted to expel a tampon held in the first member from the first member through the expulsion end of the first member.

31. The tampon applicator of claim 30, wherein the raised pattern extends a distance between 0.35 mm and 0.50 mm above the first surface.

32. The tampon applicator according to claim 31, wherein the first member comprises an elongated tube having a generally cylindrical shape.

33. The tampon applicator according to claim 30, wherein the first member is a molded thermoplastic material.

34. A tampon applicator comprising:
a. a first member capable of holding a tampon and having a shape suitable for insertion into a body cavity of a user, the first member comprising an outer surface, a longitudinal axis, an expulsion end which is adapted to expel a tampon held in the first member from the first member and a second end which is distal to the expulsion end of the first member;
b. a second member telescopically and slidably mounted in the first member In the second end of the first member, said second member adapted to expel a tampon held in the first member from the first member through the expulsion end of the first member; and
c. an insertion tip located on the expulsion end of the first member, wherein the insertion tip has a dome shape prior to use and comprises at least 3 petals, each petal extends from the expulsion end of the first member, each petal is separated from the other petals along the entirety, of each side of each petal, and the separation of each of the petals is non-linear when the petals are in the dome shape.

35. The tampon applicator of claim 34, wherein the separation of each of the petals from the other petals is not parallel with the longitudinal axis of the first member when the petals are In the dome shape.

36. The tampon applicator of claim 34, wherein the insertion tip comprises 4-6 petals.

37. The tampon applicator of claim 36, wherein the insertion tip comprises 5 petals.

38. The tampon applicator according to claim 36, wherein the first member comprises an elongated tube having a generally cylindrical shape.

39. The tampon applicator of claim 36, wherein the insertion tip and the petals of the insertion tip are integral with the first member.

40. The tampon applicator according to claim 39, wherein the first member and the Insertion tip is a molded thermoplastic material.

41. The tampon applicator according to claim 34, wherein each petal is separated from its radially-adjacent petals by a distance of about 0.75 mm to about 1.5 mm.

42. The tampon applicator according to claim 34, wherein the separation of each petal with its radially-adjacent petals is of a uniform distance.

* * * * *